United States Patent [19]

Ackrell

[11] 3,989,839
[45] Nov. 2, 1976

[54] 6,11-DIHYDRODIBENZO-THIEPIN-11-ONES, COMPOSITIONS AND USES THEREOF

[75] Inventor: Jack Ackrell, Mexico City, Mexico

[73] Assignee: Syntex (U.S.A.) Inc., Palo Alto, Calif.

[22] Filed: Aug. 13, 1975

[21] Appl. No.: 604,291

[52] U.S. Cl. .............................. 424/275; 260/327 B
[51] Int. Cl.$^2$ ....................................... C07D 337/12
[58] Field of Search ....................... 260/327 B, 333; 424/275

[56] References Cited

UNITED STATES PATENTS

| | | |
|---|---|---|
| 3,594,392 | 7/1971 | Winthrop et al..................... 260/327 |
| 3,946,036 | 3/1976 | Gadient........................... 260/327 B |

*Primary Examiner*—Henry R. Jiles
*Assistant Examiner*—C. M. S. Jaisle
*Attorney, Agent, or Firm*—Gerard A. Blaufarb; William B. Walker

[57] ABSTRACT

This invention relates to novel 6,11-dihydrodibenzo-[b.e.]-thiepin-11-ones, methods of preparation, compositions and uses thereof.

21 Claims, No Drawings

6,11-DIHYDRODIBENZO-THIEPIN-11-ONES, COMPOSITIONS AND USES THEREOF

DESCRIPTION OF THE INVENTION

This invention relates to novel 6,11-dihydrodibenzo-[b,e.]-thiepin-11-ones selected from the group of compounds represented by the formulas:

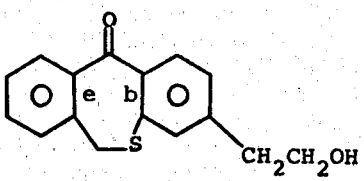

(A)

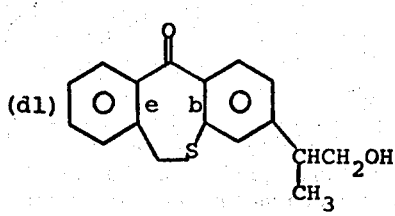

(B)

and the pharmaceutically acceptable esters and ethers thereof, methods for the preparation thereof, and compositions and methods for the use thereof.

As used in this specification and claims, the term "pharmaceutically acceptable esters" denotes those ester groups conventionally employed in this art, preferably those derived from hydrocarbon carboxylic acids or their salts. The term "hydrocarbon carboxylic acid" refers to both substituted and unsubstituted hydrocarbon carboxylic acids. These acids can be completely saturated or possess varying degrees of unsaturation (including aromatic), can be of straight chain, branched chain, or cyclic structure and preferably contain from 1 to 12 carbon atoms. Typical conventional esters, expressed as the radical, thus included within the scope of the term as defined above are acetate, propionate, 2-methylpropionate, butyrate, pentanoate, hexanoate, heptanoate, octanoate, nonanoate, dodecanoate, benzoate, 2-acetoxybenzoate, salicylate, phenylacetate, diethylacetate, trimethylacetate, t-butylacetate, cyclohexylacetate, cyclopentylpropionate, adamantoate, bicyclo[2.2.2]octyl carboxylate, hemisuccinate, hemiadipate, hemi-$\beta,\beta$-dimethylglutarate, and the like.

As used in this specification and claims, the term "pharmaceutically acceptable ether" refers to those ether groups conventionally employed in this art, preferably those derived from straight chain, branched chain, aromatic hydrocarbons and oxo heterocyclic hydrocarbons. The term "hydrocarbons" refers to both saturated and unsaturated hydrocarbons, which can be optionally substituted with groups such as hydroxy, alkoxy, halo, alkylthio, and the like. Preferably, the hydrocarbons contain from 1 to 12 carbon atoms. Typical ethers thus included within the scope of this definition include, for example, alkoxy, such as methoxy, ethoxy, propoxy, and the like; alkoxymethoxy, such as methoxymethoxy, ethoxymethoxy, and the like; tetrahydrofuran-2'-yloxy; tetrahydropyran-2'-yloxy; and 4'-alkoxytetrahydropyran-4'-yloxy, such as 4'-methoxytetrahydropyran-4'yloxy; and the like.

The novel propan-1-ols of Formula (B) and the compounds of Formulas (1), (2), and (3) wherein R is methyl, depicted below, exist as pairs of enantiomorphs, i.e., a (dl) mixture.

The novel compounds of this invention are prepared according to the reaction scheme outlined in the flow sheet which follows:

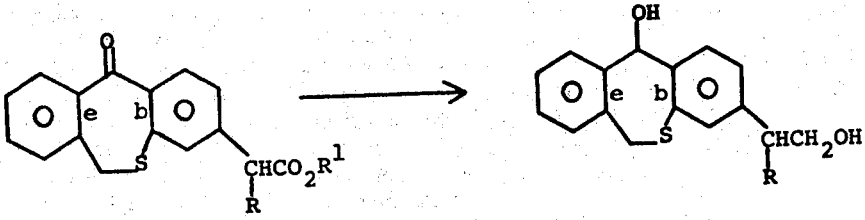

(1)            (2)

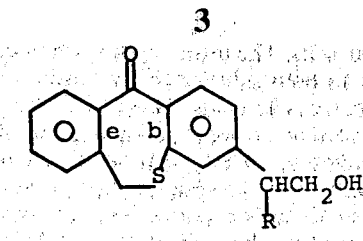

(3)

wherein R is hydrogen or methyl, and R¹ is hydrogen or an alkyl group.

The term "alkyl" refers to and includes branched and straight chain hydrocarbons containing from 1 to 12 carbon atoms. Typical alkyl groups include methyl, ethyl, propyl, isopropyl, butyl, tertiary butyl, isoamyl, neopentyl, isopentyl, hexyl, octyl, nonyl, isodecyl, 6-methyldecyl, dodecyl, and the like.

The starting compounds of Formula (1) are described in my copending application Ser. No. 591,725, filed June 30, 1975, which is hereby incorporated by reference, and made a part hereof.

The ester compounds of Formula (1), and preferably the methyl esters (R¹ = methyl), of 6,11-dihydrodibenzo-[b.e.]-thiepin-11-one-3-acetic acid and (dl)-2-(6,11-dihydrodibenzo-[b.e.]-thiepin-11-one-3-yl)propionic acid, are treated with a reducing agent to obtain the compounds of Formula (2), 2-(6,11-dihydrodibenzo-[b.e.]-thiepin-11-hydroxy-3-yl)ethan-1-ol and (dl)-2-(6,11-dihydrodibenzo-[b.e.]-thiepin-11-hydroxy-3-yl)propan-1-ol, respectively. Suitable reducing agents are lithium aluminum hydride, sodium bis(2-methoxyethoxy)aluminum hydride, diborane, and the like, with lithium aluminum hydride being preferred. The reaction is carried out in a suitable organic solvent, e.g., ether, tetrahydrofuran, dimethoxyethane, dioxane, and the like, or a combination thereof, with ether being preferred, at a temperature of from about −30° to about 30° C., about 0° to about 25° C. being preferred, for from about 5 minutes to about 2 hours, with from about 10 minutes to about 1 hour being preferred. Likewise, the free acids (R¹ = hydrogen) of Formula (1), 6,11-dihydrodibenzo-[b.e.]-thiepin-11-one-3-acetic acid and (dl)-2-(6,11-dihydrodibenzo-[b.e.]-thiepin-3-yl)propionic acid, are treated with a reducing agent, as described above, and more fully below, to obtain the corresponding alcohols of Formula (2).

The thus obtained compounds of Formula (2) are then treated with an oxidizing agent which selectively converts them to the 11-one compounds of Formula (3), i.e., 2-(6,11-dihydrodibenzo-[b.e.]-thiepin-11-one-3-yl)ethan-1-ol and (dl)-2-(6,11-dihydrodibenzo-[b.e.]-thiepin-11-one-3-yl)propan-1-ol. Suitable selective oxidizing agents are activated manganese dioxide, 2,3-dichloro-5,6-dicyano-1,4-benzoquinone, and the like, with activated manganese dioxide being preferred. The reaction is carried out in a suitable organic solvent, e.g., acetonitrile, acetone, chloroform, methylene chloride, and the like, or a combination thereof, in the presence of a small amount of an alkanol, e.g., methanol, ethanol, and the like, preferably using acetonitrile and ethanol or acetone and ethanol, at a temperature of from about 0° to about 40° C., about 20° to about 25° C. being preferred, for from about 5 minutes to about 24 hours, with from about 30 minutes to about 18 hours being preferred. This reaction, if desired, can be carried out under an inert atmosphere, e.g., a nitrogen or argon atmosphere, preferably a nitrogen atmosphere.

Upon their preparation, the alcohols of Formula (3), a composite of Formulas (A) and (B), can be converted to the corresponding esters and ethers thereof via conventional techniques.

The compounds of Formula (3) can be esterified or etherified via conventional techniques. For example, the compounds can be esterified by treatment with an acid anhydride, such as acetic anhydride, propionic anhydride, valeric anhydride, hexanoic anhydride, nonanoic anhydride, dodecanoic anhydride, caproic anhydride, and the like, in pyridine; or by treatment with an acid chloride, such as acetyl chloride, adamantoyl chloride, nonanoyl chloride and the like, in pyridine, acetonitrile and triethylamine; or by treatment with a carboxylic acid in the presence of an acid catalyst, such as p-toluenesulfonic acid, and the like.

The compounds of Formula (3) can be etherified by treatment with an alkali metal hydride, such as sodium hydride, and an organic halide, such as n-propyl bromide, 2-chlorotetrahydropyran, 2-chlorotetrahydrofuran, and the like; or by treatment with dihydrofuran, dihydropyran, 4-methoxydihydropyran, and the like, in the presence of an acid catalyst.

In each of the process steps, described herein above and below, unless otherwise indicated, the respective intermediate products are preferably separated from the reaction mixture and purified prior to their use as starting materials for the next step in the process. Such separation and purification can be effected by any suitable procedure. For example, typical separation procedures include filtration, extraction, evaporation, and typical purification procedures include crystallization, and both thin-layer and column chromatography. Optimum separation and isolation procedures can be obtained for any given step by routine experimentation as will be apparent to those skilled in this art.

Particular compounds falling within the scope of the present invention can be prepared by selecting an appropriate starting material, for example, from those referred to above, and then selecting particular reaction step or steps, as for example described above, to give the compound desired. In view of this disclosure, the preparation of particular compounds, including compounds falling within the present invention but not specifically described in this specification, will be apparent to those skilled in this art.

Exemplary of the compounds of the present invention, as represented by the Formula (3) above, which as noted above is a composite of Formulas (A) and (B), and the pharmaceutically acceptable esters and ethers thereof, are the following illustrative compounds:

2-(6,11-dihydrodibenzo-[b.e.]-thiepin-11-one-3-yl)ethan-1-ol, 2-(6,11-dihydrodibenzo-[b.e.]-thiepin-11-one-3-yl)ethan-1-ol acetate, 2-(6,11-dihydrodibenzo-[b.e.]-thiepin-11-one-3-yl)ethan-1-ol propionate, 2-(6,11-dihydrodibenzo-[b.e.]-thiepin-11-one-3-yl)ethan-1-ol hexanoate, 2-(6,11-dihydrodibenzo-[b.e.]-thiepin-11-one-3-yl)ethan-1-ol nonanoate, 2-(6,11-dihydrodibenzo-[b.e.]-thiepin-11-one-3-yl)ethan-1-ol dodecanoate, 2-(6,11-dihydrodibenzo-[b.e.]-thiepin-11-one-3-yl)ethan-1-ol tetrahydropyran-2'-yl ether, 2-(6,11-dihydrodibenzo-[b.e.]-thiepin-11-one-3-yl)ethan-1-ol tetrahydrofuran-2'-yl ether, (dl)-2-(6,11-dihydrodibenzo-[b.e.]-thiepin-11-one-3-yl)propan-1-ol, (dl)-2-(6,11-dihydrodibenzo-[b.e.]-thiepin-11-one-3-yl)propan-1-ol acetate, (dl)-2-(6,11-dihydrodibenzo-[b.e.]-thiepin-11-one-3-yl)propan-1-ol propionate, (dl)-2-(6,11-dihydrodibenzo-[b.e.]-thiepin-11-one-3-yl)propan-1-ol hexanoate, (dl)-2-(6,11-dihydrodibenzo-[b.e.]-thiepin-11-one-3-yl)propan-1-ol nonanoate, (dl)-2-(6,11-dihydrodibenzo-[b.e.]-thiepin-11-one-3-yl)propan-1-ol dodecanoate, (dl)-2-(6,11-dihydrodibenzo-[b.e.]-thiepin-11-one-3-yl)propan-1-ol tetrahydropyran-2'-yl ether, and (dl)-2-(6,11-dihydrodibenzo-[b.e.]-thiepin-11-one-3-yl)propan-1-ol tetrahydrofuran-2'-yl ether.

The compounds of Formulas (A) and (B), Formula (3) being a composite thereof, are useful as anti-inflammatory agents, platelet aggregation inhibitors, fibrinolytic agents, and as smooth muscle relaxants. The compounds of Formulas (A) and (B) can be used both prophylactically and therapeutically.

The compounds of Formulas (A) and (B) exhibit anti-inflammatory, analgesic and anti-pyretic activities. Accordingly, the compositions containing these compounds are useful in the treatment and elimination of inflammation such as inflammatory conditions of the muscular skeletal system, skeletal joints and other tissues, for example, in the treatment of inflammatory conditions such as rheumatism, concussion, laceration, arthritis, bone fractures, post-traumatic conditions, and gout. In those cases in which the above conditions include pain and pyrexia coupled with inflammation, the instant compounds are useful for the relief of these conditions as well as the inflammation.

Administration of the active compound of Formulas (A) and (B) in an appropriate pharmaceutical composition can be via any of the accepted modes of administration of agents for the treatment of inflammation, pain, or pyrexia, or the prophylaxis thereof. Thus, administration can be for example, orally, parenterally, or topically, in the form of solid, semi-solid or liquid dosage forms, such as, for example, tablets, suppositories, pills, capsules, powders, liquids, suspensions, creams, lotions, ointments, or the like, preferably in unit dosage forms suitable for simple administration of precise dosages. The compositions will include a conventional pharmaceutical carrier or excipient and an active compound of Formulas (A) and (B), and, in addition, may include other medicinal agents, pharmaceutical agents, carriers, adjuvants, etc.

The preferred manner of administration, for the conditions detailed above, is oral using a convenient daily dosage regimen which can be adjusted according to the degree of affliction. Generally, a daily dose of from 0.1 mg. to 50 mg. of the active compound of Formulas (A) and (B) per kilogram of body weight is used. Most conditions respond to treatment comprising a dosage level of the order of 2 mg. to 15 mg. per kilogram of body weight per day. For such oral administration, a pharmaceutically acceptable non-toxic composition is formed by the incorporation of any of the normally employed excipients, such as, for example, pharmaceutical grades of mannitol, lactose, starch, magnesium stearate, sodium saccharin, talcum, cellulose, glucose, sucrose, magnesium carbonate, and the like. Such compositions take the form of solutions, suspensions, tablets, pills, capsules, powders, sustained release formulations and the like.

The active compounds of Formulas (A) and (B) may be formulated into a suppository using, for example, polyalkylene glycols, for example, propylene glycol, as the carrier. Liquid pharmaceutically administerable compositions can, for example, be prepared by dissolving, dispersing, etc. an active compound of Formula I and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of non-toxic auxiliary substances such as wetting or emulsifying agents, pH buffering agents and the like, such as for example, sodium acetate, sorbitan monolaurate, triethanolamine oleate, etc.

Actual methods of preparing such dosage forms are known, or will be apparent, to those skilled in this art; for example, see Remington's *Pharmaceutical Sciences*, Mack Publishing Company, Easton, Pennsylvania, 14th. Edition, 1970. The composition to be administered will, in any event, contain a quantity of the active compound(s) in a pharmaceutically effective amount for relief of the particular condition being treated in accordance with the teachings of this invention.

The compounds of Formulas (A) and (B) described above are also uterine smooth muscle relaxants and thus are useful as agents for maintaining the pregnancy of pregnant mammals, for the benefit of the mother and/or the fetus, until termination of the pregnancy is considered, from a medical point of view, to be favorable, or more favorable, for the mother and/or the fetus. It should be understood, however, that in certain instances, for example where parturition has already begun (i.e., the mother is experiencing uterine contractions, especially near full term), that administration of the compounds herein described may not maintain the pregnant state for an indefinite period of time. Rather, in such instances, the pregnancy will, most probably, be slightly "prolonged", a factor which may be advantageous to either the mother and/or the fetus.

In particular, the compounds of Formulas (A) and (B) are used as agents for delaying the onset of, or for postponing, parturition. As used in this application, the phrase "to delay the onset of parturition" is intended to cover the delay in parturition caused by the administration of the compounds of Formula(s) (A) and (B) at any time before uterine muscle contractions have begun. Thus, it is intended that the aforementioned phrase cover abortion prevention early in pregnancy (i.e., before the fetus is "viable") as well as delaying premature parturition, a term which sometimes is used with reference to that premature labor experienced later in the pregnancy when the fetus is considered to be "viable". In either case, the agents are administered as prophylatic agents in that such administration tends to prevent the onset of parturition. This administration is particularly useful in the treatment of women having a history of spontaneous abortion, miscarriage or premature delivery (i.e., delivery prior to full term). Such administration is also useful where there are clinical indications thaat the pregnancy might be terminated prior to that time and is considered favorable to the mother and/or fetus.

With respect to animals, this treatment can also be utilized to synchronize the deliveries from a group of pregnant animals to happen at or about the same time, or to happen at or about a desired time and/or place, when the births can be handled with greater facility.

As used in this application, the phrase "postponing parturition" is intended to cover that delay in parturition caused by the administration of the compounds of Formulas (A) and (B) after uterine muscle contractions have begun. The condition of the patient, including the time within the gestation period when the contractions have begun, the severity of the contractions and how long the contractions have taken place will affect the results achieved with the administration of the compounds of Formulas (A) and (B). For example, the effect can be to reduce the intensity and/or the duration of the contractions (the actual act of parturition being "prolonged"), or to stop the contractions altogether. In either case, the effect will be to prolong the gestation period although, depending upon the condition of the patient as described above, the effect may either be slight or, under appropriate circumstances, somewhat greater. Such administration may be to prevent spontaneous abortion, to cause the delivery to be more easily accomplished and/or less painful to the mother, or to occur at a more appropriate time and/or place.

In all cases, administration of the compounds of Formulas (A) and (B), for the purposes set forth herein, should be consistent with best and/or accepted medical (or veterinary) practices so as to maximize the benefits to the mother and the fetus. For example, administration should not be continued so long past full term that the fetus dies in utero.

In the practice of the methods of the present invention, a therapeutically effective amount of a compound of Formulas (A) and (B), or a pharmaceutical composition containing a compound of Formulas (A) and (B), is administered to the pregnant mammal via any of the usual and acceptable methods known in the art. The compound can be administered either singly or in combination with another compound or compounds, as defined above, or other pharmaceutical agents, carriers, adjuvants, etc. Such compounds(s) or compositions can be administered orally, parenterally, either in the form of solid, semi-solid, or liquid dosage forms. Typically, administration is by a pharmaceutical composition containing the pharmaceutically active compound and one or more pharmaceutical carriers or adjuvants.

The administerable pharmaceutical composition may take the form of oral tablets, vaginal or uterine tablets or suppositories, pills, capsules, liquid solutions, suspensions, or the like, preferably in unit dosage forms suitable for simple administration of precise dosages. Conventional non-toxic solid carriers include, for example, pharmaceutical grades of mannitol, lactose, starch, magnesium stearate, sodium saccharin, talcum, cellulose, glucose, sucrose, magnesium carbonate, and the like. The active compound as defined above may be formulated as suppositories using, for example, polyalkylene glycols, for example, propylene glycol, as the carrier. Liquid pharmaceutically administerable compositions can, for example, be prepared by dissolving, dispersing, etc. an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of non-toxic auxiliary substances such as wetting or emulsifying agents, pH buffering agents and the like, for example, sodium acetate, sorbitan monolaurate, triethanolamine oleate, etc. Actual methods of preparing such dosage forms are known, or will be apparent, to those skilled in this art; for example, see Remington's *Pharmaceutical Sciences*, Mack Publishing Company, Easton, Pennsylvania, 14th. Edition, 1970. The composition or formulation to be administered will, in any event, contain a quantity of the active compound(s) in an amount effective to delay the onset of parturition or to postpone parturition if uterine contractions have already begun. Generally a daily dose of from about 10 mg. to about 250 mg. of the active compound per kilogram of body weight will be administered, with administration being a single daily dose or up to three or four smaller doses regularly given throughout the day. The amount of active compound administered will, of course, depend on its relative activity.

DESCRIPTION OF SPECIFIC EMBODIMENTS

The following specific description, recited in the examples below, is given to enable those skilled in this art to more clearly understand and practice the present invention. It should not be considered as a limitation upon the scope of the invention but merely as being illustrative and representative thereof.

Where necessary, examples are repeated to prepare additional material for later examples. By the term room temperature is meant from about 20° to about 25° C.

EXAMPLE 1

A. 2.1 G. of methyl 6,11-dihydrodibenzo-[b.e.]-thiepin-11-one-3-acetate (1) in 350 ml. of ether is added to a stirred solution of 1.1 g. of lithium aluminum hydride in 200 ml. of ether at −20° C. After 10 minutes 10 ml. of ethyl acetate and then 50 ml. of water is added. The organic layer is separated, dried over magnesium sulfate and the solvents removed under reduced pressure to give a residue which is crystallized from ethyl acetate:ether (1:3) to yield 1.25 g. of 2-(6,11-dihydrodibenzo-[b.e.]-thiepin-11-hydroxy-3-yl)ethan-1-ol (2). The mother liquors are taken to dryness by evaporation and the residue obtained is crystallized from 5 ml. of benzene to yield an additional 0.45 g. of 2-(6,11-dihydrodibenzo-[b.e.]-thiepin-11-hydroxy-3-yl)ethan-1-ol (2). A sample of 2-(6,11-dihydrodibenzo-[b.e.]-thiepin-11-hydroxy-3-yl)ethan-1-ol (2), taken from the combined crystal crops, has a melting point of 131°–132° C.

Similarly, substituting a stoichiometrically equivalent amount of methyl (dl)-2-(6,11-dihydrodibenzo-[b.e.]-thiepin-11-one-3-yl)propionate, for methyl 6,11-dihydrodibenzo-[b.e.]-thiepin-11-one-3-acetate, is productive of (dl)-2-(6,11-dihydrodibenzo-[b.e.]-thiepin-11-hydroxy-3-yl)propan-1-ol, In like manner substituting the other esters, e.g., the ethyl, propyl, isopropyl, butyryl, isobutyryl, amyl, isoamyl, hexyl, isohexyl, nonanyl, decanyl, dodecanyl, and the like, of 6,11-dihydrodibenzo-[b.e.]-thiepin-11-one-3-acetic acid or (dl)-2-(6,11-dihydrodibenzo-[b.e.]-thiepin-11-one-3-yl)propionic acid, is productive of 2-(6,11-dihydrodibenzo-[b.e.]-thiepin-11-hydroxy-3-yl)ethan-1-ol or (dl)-2-(6,11-dihydrodibenzo-[b.e.]-thiepin-11-hydroxy-3-yl)propan-1-ol, respectively.

B. 2.09 G. of (dl)-2-(6,11-dihydrodibenzo-[b.e.]-thiepin-11-one-3-yl)propionic acid (1) in 100 ml. of ether is slowly added to a solution of 1.0 g. of lithium aluminium hydride in 100 ml. of ether. After 1 hour at 25° C., the reaction mixture is cooled to −20° C., and 10 ml. of ethyl acetate is added. The mixture is allowed to warm to room temperature followed by the sequential addition of 2 ml. of water, 2 ml. of 50% aqueous potassium hydroxide and 5 ml. of water. After stirring for 20 minutes, the mixture is filtered and the filtrate evaporated to dryness to yield 1.88 g. of (dl)-2-(6,11-dihydrodibenzo-[b.e.]-thiepin-11-hydroxy-3-yl)propan-1-ol (2), a white foam, having a melting point of 70°-80° C.

Similarly, substituting a stoichiometrically equivalent amount of 6,11-dihydrodibenzo-[b.e.]-thiepin-11-one-3-acetic acid, for (dl)-2-(6,11-dihydrodibenzo-[b.e.]-thiepin-11-one-3-yl)propionic acid, is productive of 2-(6,11-dihydrodibenzo-[b.e.]-thiepin-11-hydroxy-3-yl)ethan-1-ol.

EXAMPLE 2

A. 0.7 G. of 2-(6,11-dihydrodibenzo-[b.e.]-thiepin-11-hydroxy-3-yl)ethan-1-ol (2) in 50 ml. of acetonitrile and 0.5 ml. of ethanol is stirred, under nitrogen, at room temperature, with 7 g. of activated manganese dioxide. After 18 hours the reaction mixture is filtered and washed with 100 ml. of chloroform. Evaporation of the filtrate and drying at 70°C. (0.2 mm) yields 700 mg. of 2-(6,11-dihydrodibenzo-[b.e.]-thiepin-11-one-3-yl)ethan-1-ol (3), an oily crystalline solid, IR: $\nu_{max}^{CHCl_3}$ 3630, 1645, 1600 cm$^{-1}$; NMR: $\delta_{TMS}^{CDCl_3}$ 1.62 ($s$, 1H), 2.80 ($t$, 2H), 3.80 ($t$, 2H), 3.98 ($s$, 2H), 6.9–7.6 ($m$, 6H) 8.11 p.p.m. ($d$, H).

B. 1.36 G. of (dl)-2-(6,11-dihydrodibenzo-[b.e.]-thiepin-11-hydroxy-3-yl)propan-1-ol (2) in 250 ml. of acetone containing 1 ml. of ethanol is treated with 10 g. of activated manganese dioxide at room temperature. The reaction mixture is stirred for 40 minutes, then filtered and the manganese dioxide washed with 75 ml. of acetone. The filtrate is evaporated to dryness to yield 1.3 g. of (dl)-2-(6,11-dihydrodibenzo-[b.e.]-thiepin-11-one-3-yl)propan-1-ol (3), a pale yellow oil, UV: $\lambda_{max}^{CH_3OH}$ 250, 279, 350 nm. ($\epsilon$ 21,900, 10,200, 3900); IR: $\nu_{max}^{CHCl_3}$ 3635, 1645, 1600 cm$^{-1}$; NMR: $\delta_{TMS}^{CDCl_3}$ 1.23 ($d$, 3H), 1.63 ($s$, 1H), 2.95 ($m$, 1 H), 3.63 ($d$, 2H), 3.98 ($s$, 2H), 6.90–7.60 ($m$, 6H), 8.10 p.p.m. ($d$, 1H).

EXAMPLE 3

(Preparation of Esters)

A. 340 Mg. of 2-(6,11-dihydrodibenzo-[b.e.]-thiepin-11-one-3-yl)ethan-1-ol (3) in 1 ml. of pyridine is treated, under nitrogen, at room temperature, with 300 mg. of acetic anhydride. After 60 hours, the reaction mixture is quenched with water, acidified with aqueous hydrochloric acid, and extracted with benzene (2 × 20 ml.). The extracts are combined, dried over magnesium sulfate and the solvent is removed under reduced pressure to give a residue which is rechromatographed on 20 g. of silica gel and eluted with chloroform:hexane (1:1) to yield 200 mg. of 2-(6,11-dihydrodibenzo-[b.e.]-thiepin-11-one-3-yl)ethan-1-ol acetate, which upon recrystallization from dichloromethane:ether (1:5) melts at 94°–94.5° C.

B. 350 Mg. of 2-(6,11-dihydrodibenzo-[b.e.]-thiepin-11-one-3-yl)ethan-1-ol (3) in 1 ml. of pyridine is treated, under nitrogen, at room temperature, with 200 mg. of propionic anhydride. After 3 hours, the reaction mixture is quenched with water and extracted with benzene (2 × 20 ml.). The benzene extracts are combined, dried over magnesium sulfate, the solvent is removed under reduced pressure and the residue is chromatographed on silica gel and eluted with chloroform:hexane (2:3). After recrystallization from methanol there is obtained 285 mg. of 2-(6,11-dihydrodibenzo-[b.e.]-thiepin-11-one-3-yl)ethan-1-ol propionate, having a melting point of 85°–86° C.

C. 255 Mg. of 2-(6,11-dihydrodibenzo-[b.e.]-thiepin-11-one-3-yl)ethan-1-ol (3) in 1 ml. of pyridine is treated, under nitrogen, at room temperature, with 220 mg. of hexanoic anhydride. After 60 hours, the reaction mixture is quenched with water, acidified with aqueous hydrochloric acid, and extracted with benzene (2 × 20 ml.). The extracts are combined, dried over magnesium sulfate and the solvent is removed under reduced pressure to give a residue which is chromatographed on 20 g. of silica gel and eluted with chloroform:hexane (1:1). The eluate is taken to dryness by evaporation and the residue obtained is taken up in 10 ml. of ether and stirred for 10 minutes with 1 ml. of 10% aqueous sodium carbonate. The ether layer is separated, dried over magnesium sulfate, and the solvent removed under reduced pressure to yield 257 mg. of 2-(6,11-dihydrodibenzo-[b.e.]-thiepin-11-one-3-yl)ethan-1-ol hexanoate, a pale yellow oil, IR $\nu_{max}^{film}$ 1730, 1650, 1600 cm$^{-1}$; NMR: $\delta_{TMS}^{CDCl_3}$ 0.82 ($m$, 3H), 1.0–1.70 ($m$, 6H), 2.22 ($t$, 2H), 2.84 ($t$, 2H), 3.99 ($s$, 2H), 4.23 ($t$, 2H), 6.9–7.7 ($m$, 6H), 8.09 p.p.m. ($d$, 1H).

D. 255 Mg. of 2-(6,11-dihydrodibenzo-[b.e.]-thiepin-11-one-3-yl)ethan-1-ol (3) in 1 ml. of pyridine is treated, under nitrogen, at room temperature, with 250 mg. of nonanoyl chloride. After 60 hours, the reaction mixture is quenched with water, acidified with aqueous hydrochloric acid, and extracted with benzene (2 × 20 ml.). The extracts are combined, washed with 10 ml. of 10% aqueous sodium carbonate, dried over magnesium sulfate and the solvent is removed under reduced pressure to give a residue which is chromatographed on 20 g. of silica gel and eluted with chloroform:hexane (1:1) to yield 225 mg. of 2-(6,11-dihydrodibenzo-[b.e.]-thiepin-11-one-3-yl)ethan-1-ol nonanoate, a pale yellow oil, IR: $\nu_{max}^{film}$ 1730, 1650, 1600 cm$^{-1}$; NMR: $\delta_{TMS}^{CDCl_3}$ 0.83 ($t$, 3H), 1.0–1.70 ($b.s.$, 12H), 2.22 ($t$, 2H), 2.85 ($t$, 2H), 3.88 ($s$, 2H), 4.20 ($t$, 2H), 6.90–7.60 ($m$, 6H), 8.05 p.p.m. ($d$, 1H).

E. 300 Mg. of 2-(6,11-dihydrodibenzo-[b.e.]-thiepin-11-one-3-yl)ethan-1-ol (3) in 2 ml. of pyridine is treated, under nitrogen, at room temperature, with 300 mg. of dodecanoyl chloride. After 8 hours, the reaction mixture is quenched with water and extracted with benzene (2 × 20 ml.). The extracts are combined, washed with 10 ml. of 10% aqueous sodium carbonate and dried over magnesium sulfate. The solvent is removed under reduced pressure and the residue chromatographed on 20 g. of silica gel and eluted with chloroform:hexane (1:2) to yield 315 dmg. of 2-(6,11-dihydrodibenzo-[b.e.]-thiepin-11-one-3-yl)ethan-1-ol dodecanoate, a pale yellow oil, UV $\lambda_{max}^{CH_3OH}$ 249, 279, 352 mm. ($\epsilon$ 20,400, 9100, 2800); IR: $\nu_{max}^{film}$ 1740, 1645, 1600 cm.$^{-1}$; NMR: $\delta_{TMS}^{CDCl_3}$ 0.83 ($t$, 3H), 1.24 ($s$, 18H), 2.23 ($t$, 2H), 2.88 ($t$, 2H), 3.98 ($s$, 2H), 4.25 ($t$, 2H), 7.00–7.70 ($m$, 6H), 8.10 p.p.m. ($d$, 1H).

F. 250 Mg. of (dl)-2-(6,11-dihydrodibenzo-[b.e.]-thiepin-11-one-3-yl)propan-1-ol (3) in 1 ml. of pyridine is treated, under nitrogen, at room temperature, with 250 mg. of acetic anhydride. After 18 hours, the reaction mixture is quenched with water and is extracted with benzene (2 × 20 ml.). The extracts are combined, dried over magnesium sulfate, evaporated to dryness and the residue is chromatographed on 30 g. of silica gel and eluted with hexane:ethyl acetate (8:1) to yield 249 mg. of (dl)-2-(6,11-dihydrodibenzo-[b.e.]-thiepin-11-one-3-yl)propan-1-ol acetate, a pale yellow oil, UV: $\lambda_{max}.^{CH_3OH}$ 246, 278, 352 nm. ($\epsilon$ 21,400, 8500, 2800); IR: $\nu_{max}.^{film}$ 1735, 1645, 1600 cm.$^{-1}$; NMR: $\delta_{TMS}^{CDCl_3}$ 1.25 (d, 3H), 1.95 (s, 3H), 2.80–3.40 (m, 1H), 3.98 (s, 2H), 4.10 (d, 2H), 6.90–7.60 (m, 6H), 8.09 p.p.m. (d, 1H).

G. 250 Mg. of (dl)-2-(6,11-dihydrodibenzo-[b.e.]-thiepin-11-one-3-yl)propan-1-ol (3) in 1.5 ml. of pyridine is treated, under nitrogen, at room temperature, with 300 mg. of propionic anhydride. After 18 hours, the reaction mixture is quenched with water and is extracted with benzene (2 × 20 ml.). The extracts are combined, dried over magnesium sulfate, evaporated to dryness and the residue is chromatographed on 30 g. of silica gel and eluted with hexane:ethyl acetate (9:1) to yield 253 mg. of (dl)-2-(6,11-dihydrodibenzo-[b.e.]-thiepin-11-one-3-yl)propan-1-ol propionate, a pale yellow oil, UV: $\lambda_{max}.^{CH_3OH}$ 250, 278, 352 nm. ($\epsilon$18,200, 8300, 2800), IR: $\nu_{max}.^{film}$ 1740, 1645, 1600 cm$^{-1}$; NMR: $\delta_{TMS}^{CDCl_3}$ 1.05 (t 3H), 1.26 (d, 3H), 2.23 (q, 2H), 3.02 (m, 1H), 4.00 (s, 2H), 4.10 (d, 2H), 6.90–7.60 (m, 6H), 8.10 p.p.m. (d, 1H).

H. 240 Mg. of (dl)-2-(6,11-dihydrodibenzo-[b.e.]-thiepin-11-one-3-yl)propan-1-ol (3) in 1 ml. of pyridine is treated, under nitrogen, at room temperature, with 180 mg. of hexanoic anhydride. After 18 hours, the reaction mixture is quenched with water and extracted with benzene (2 × 20 ml.). The extracts are combined and washed with 10 ml. of 10% of aqueous sodium carbonate, dried over magnesium sulfate and evaporated under reduced pressure. The residue is chromatographed on 30 g. of silica gel and eluted with hexane:ethyl acetate (10:1) to yield 241 mg. of (dl)-2-(6,11-dihydrodibenzo-[b.e.]-thiepin-11-one-3-yl)propan-1-ol hexanoate, a pale yellow oil, UV: $\lambda_{max}.^{CH_3OH}$ 248, 280, 350 nm. ($\epsilon$21,400, 9300, 2800); IR: $\nu_{max}.^{film}$ 1740, 1645, 1600 cm$^{-1}$; NMR: $\delta_{TMS}^{CDCl_3}$ 0.78 (t, 3H), 1.00–1.63 (m, 9H), 2.15 (t, 2H), 3.02 (m, 1H), 3.94 (s, 2H), 4.05 (d, 2H), 6.80–7.60 (m, 6H), 8.00 p.p.m. (d, 1H).

I. 250 Mg. of (dl)-2-(6,11-dihydrodibenzo-[b.e.]-thiepin-11-one-3-yl)propan-1-ol (3) in 1 ml. of pyridine is treated, under nitrogen, at room temperature, with 250 mg. of dodecanoyl chloride. After 18 hours, the reaction mixture is quenched with water and is then extracted with benzene (2 × 20 ml.). The extracts are combined, washed with 10 ml. of 10% aqueous sodium carbonate, dried over magnesium sulfate and evaporated to dryness under reduced pressure. The residue is chromatographed on 30 g. of silica gel and eluted with hexane:ethyl acetate (9:1) to yield 250 mg. of (dl)-2-(6,11-dihydrodibenzo-[b.e.]-thiepin-11-one-3-yl)propan-1-ol dodecanoate, a pale yellow oil, UV: $\lambda_{max}.^{CH_3OH}$ 250, 280, 350 nm, ($\nu$21,400, 9300, 2600); IR: $\nu_{max}.^{film}$ 1740, 1645, 1600 cm$^{-1}$; NMR: $\delta_{TMS}^{CDCl_3}$ 0.92 (t, 3H), 1.21 (s, 2H), 2.20 (t, 2H), 3.11 (m, 1H), 4.0 (s, 2H), 4.11 (d, 2H), 6.90–7.60 (m, 6H), 8.10 p.p.m. (d, 1H).

In like manner, substituting other appropriate acid anhydrides or acid chlorides, with 2-(6,11-dihydrodibenzo-[b.e.]-thiepin-11-one-3-yl)ethan-1-ol or (dl)-2-(6,11-dihydrodibenzo-[b.e.]-thiepin-11-one-3-yl)propan-1-ol is productive of, for example, 2-(6,11-dihydrodibenzo-[b.e.]-thiepin-11-one-3-yl)ethan-1-ol heptanoate,
2-(6,11-dihydrodibenzo-[b.e.]-thiepin-11-one-3-yl)ethan-1-ol butyrate,
2-(6,11-dihydrodibenzo-[b.e.]-thiepin-11-one-3-yl)ethan-1-ol isobutyrate, and the like; and
(dl)-2-(6,11-dihydrodibenzo-[b.e.]-thiepin-11-one-3-yl)propan-1-ol heptanoate,
(dl)-2-(6,11-dihydrodibenzo-[b.e.]-thiepin-11-one-3-yl)propan-1-ol butyrate,
(dl)-2-(6,11-dihydrodibenzo-[b.e.]-thiepin-11-one-3-yl)propan-1-ol isobutyrate, and
(dl)-2-(6,11-dihydrodibenzo-[b.e.]-thiepin-11-one-3-yl)propan-1-ol nonanoate, and the like, respectively.

EXAMPLE 4

(Preparation of Ethers)

A. 240 Mg. of 2-(6,11-dihydrodibenzo-[b.e.]-thiepin-11-one-3-yl)ethan-1-ol (3) is dissolved in 20 ml. of ether, and to the solution is added 0.5 ml. of dihydropyran and 50 mg. of p-toluenesulfonic acid. After 24 hours, 200 mg. of triethylamine is added. The solution is then poured into water and extracted with ethyl acetate. The extract is dried over sodium sulfate, evaporated and the residue chromatographed on silica gel, eluting with hexane:ethyl acetate (9:1), to yield 245 mg. of 2-(6,11-dihydrodibenzo-[b.e.]-thiepin-11-one-3-yl)ethan-1-ol tetrahydropyran-2'-yl ether, a pale yellow oil, UV: $\lambda_{max}.^{CH_3OH}$ 250, 280, 350 nm. ($\epsilon$ 17,500, 7700, 2300); IR: $\nu_{max}.^{CHCl_3}$ 1645, 1600 cm$^{-1}$, NMR: $\delta_{TMS}^{CDCl_3}$ 1.60 (b,s, 6H), 2.82 (t, 2H), 3.20–3.90 (m, 4H), 3.98 (s, 2H), 4.50 (b,m, 1H), 6.98–7.60 (m, 6H), 8.08 p.p.m. (d, 1H).

B. 250 Mg. of (dl)-2-(6,11-dihydrodibenzo-[b.e.]-thiepin-11-one-3-yl)propan-1-ol (3) is dissolved in 70 ml. of ether and to the solution is added 1 ml. of dihydropyran and 200 mg. of p-toluenesulfonic acid. After 3½ hours a few drops of triethylamine are added and the solution is washed with water, dried with magnesium sulfate and evaporated under reduced pressure. The residue is chromatographed on 40 g. of silica gel and eluted with hexane:ethyl acetate (20:1) to yield 150 mg. of (dl)-2-(6,11-dihidrodibenzo-[b.e.]-thiepin-11-one-3-yl) propan-1-ol tetrahydropyran-2'-yl ether, a pale yellow oil, UV: $\lambda_{max}.^{CH_3OH}$ 248, 280, 350 nm. ($\epsilon$ 17,000, 7600, 3470); IR: $\nu_{max}.^{CHCH_3}$ 1645, 1600 cm$^{-1}$; NMR: $\delta_{TMS}^{CDCl_3}$ 1.27 (d, 3H), 1.55 (b,s, 6H), 2.80–3.90 (m, 4H), 4.0 (s, 2H), 4.50 (b,m, 1H), 6.90–7.70 (m, 6H), 8.10 p.p.m. (d, 1H).

In like manner, substituting other ether forming compounds, e.g., dihydrofuran and 4-methoxydihydropyran, for dihydropyran, with 2-(6,11-dihydrodibenzo-[b.e.]-thiepin-11-one-3-yl)ethan-1-ol or (dl)-2-(6,11-dihydrodibenzo-[b.e.]-thiepin-11-one-3-yl)propan-1-ol, is productive, of for example, 2-(6,11-dihydrodibenzo-[b.e.]-thiepin-11-one-3-yl)ethan-1-ol tetrahydrofuran-2'-yl ether, and
2-(6,11-dihydrodibenzo-[b.e.]-thiepin-11-one-3-yl)ethan-1-ol 4'-methoxytetrahydropyran-4'-yl ether; and (dl)-2-(6,11-dihydrodibenzo-[b.e.]-thiepin-11-one-
3-yl)propan-1-ol tetrahydrofuran-2'-yl ether, and
(dl)-2-(6,11-dihydrodibenzo-[b.e.]-thiepin-
11-one-3-yl)propan-1-ol 4'-methoxytetrahydropy-
ran-4'-yl ether, respectively.

EXAMPLE 5

(Preparation of Ethers)

0.27 G. of 2-(6,11-dihydrodibenzo-[b.e.]-thiepin-11-one-3-yl)ethan-1-ol (3) is added to 60 mg. of 50% sodium hydride (previously washed with hexane to remove mineral oil) in 15 ml. of dry dimethylformamide. After hydrogen evolution ceases 135 mg. of n-propyl bromide is added and the resulting mixture is heated at reflux, in an argon atmosphere. The reaction is monitored by thin layer chromatography, and when complete, the volume is reduced to about 3 ml. by evaporation, 20 ml. of water is added, and the product is extracted with ethyl acetate (2 × 20 ml). The extracts are combined and the ethyl acetate is removed under reduced pressure to give a residue which is dissolved in benzene and chromatographed on a column containing 6 g. of neutral alumina, eluting with mixtures of hexane-benzene and finally pure benzene. Those fractions which, by thin layer chromatography, show the presence of the desired product are combined and evaporated to dryness to yield 2-(6,11-dihydrodibenzo-[b.e.]-thiepin-11-one-3-yl)ethan-1-ol n-propyl ether.

Similarly, substituting a stoichiometrically equivalent amount of (dl)-2-(6,11-dihydrodibenzo-[b.e.]-thiepin-11-one-3-yl)propan-1-ol, for 2-(6,11-dihydrodibenzo-[b.e.]-thiepin-b 11-one-3-yl)ethan-1-ol, is productive of (dl)-2-(6,11-dihydrodibenzo-[b.e.]-thiepin-11-one-3-yl)propan-1-ol n-propyl ether.

In like manner, substituting other organic halides, e.g., cyclopentyl bromide, hexyl iodide, and ethyl iodide, for n-propyl bromide, with 2-(6,11-dihydrodibenzo-[b.e.]-thiepin-11-one-3-yl)ethan-1-ol or (dl)-2-(6,11-dihydrodibenzo-[b.e.]-thiepin-11-one-3-yl)propan-1-ol, is productive, of for example, 2-(6,11-dihydrodibenzo-[b.e.]-thiepin-11-one-3-yl)ethan-1-ol cyclopentyl ether,
2-(6,11-dihydrodibenzo-[b.e.]-thiepin-11-one-3-yl)ethan-1-ol hexyl ether, and
2-(6,11-dihydrodibenzo-[b.e.]-thiepin-11-one-3-yl)ethan-1-ol ethyl ether; and
(dl)-2-(6,11-dihydrodibenzo-[b.e.]-thiepin-11-one-3-yl)propan-1-ol cyclopentyl ether,
(dl)-2-(6,11-dihydrodibenzo-[b.e.]-thiepin-11-one-3-yl-propan-1-ol hexyl ether, and
(dl)-2-(6,11-dihydrodibenzo[b.e.]-thiepin-11-one-3-yl)propan-1-ol ethyl ether, respectively.

EXAMPLE 6

| Ingredients | Quantity Per Tablet, mgs. |
| --- | --- |
| 2-(6,11-dihydrodibenzo-[b.e.]-thiepin-11-one-3-yl)ethan-1-ol | 150 |
| cornstarch | 40 |
| sucrose | 200 |

The above ingredients are thoroughly mixed and pressed into single scored tablets.

EXAMPLE 7

| Ingredients | Quantity Per Tablet, mgs. |
| --- | --- |
| 2-(6,11-dihydrodibenzo-[b.e.]-thiepin-11-one-3-yl)ethan-1-ol | 150 |
| cornstarch | 100 |
| lactose | 393 |
| magnesium stearate | 2 |

The above ingredients are mixed intimately and pressed into single scored tablets.

EXAMPLE 8

| Ingredients | Quantity Per Capsule, mgs. |
| --- | --- |
| 2-(6,11-dihydrodibenzo-[b.e.]-thiepin-11-one-3-yl)ethan-1-ol | 150 |
| lactose | 190 |

The above ingredients are mixed and introduced into a hardshell gelatin capsule.

EXAMPLE 9

| Ingredients | Quantity Per Capsule, mgs. |
| --- | --- |
| 2-(6,11-dihydrodibenzo-[b.e.]-thiepin-11-one-3-yl)ethan-1-ol acetate | 150 |
| lactose | 182 |
| magnesium stearate | 8 |

The above ingredients are mixed and introduced into a hardshell gelatin capsule.

EXAMPLE 10

| Ingredients | Quantity Per Tablet, mgs. |
| --- | --- |
| 2-(6,11-dihydrodibenzo-[b.e.]-thiepin-11-one-3-yl)ethan-1-ol propionate | 150 |
| cornstarch | 100 |
| lactose | 370 |
| magnesium stearate | 2 |

The above ingredients are mixed intimately and pressed into single scored tablets.

EXAMPLE 11

| Ingredients | Quantity Per Capsule, mgs. |
| --- | --- |
| 2-(6,11-dihydrobenzo-[b.e.]-thiepin-11-one-3-yl)ethan-1-ol hexanoate | 250 |
| lactose | 225 |

The above ingredients are mixed and introduced into a No. 1 hardshell gelatin capsule.

EXAMPLE 12

| Ingredients | Quantity Per Tablet, mgs. |
| --- | --- |
| 2-(6,11-dihydrodibenzo-[b.e.]-thiepin-11-one-3-yl)ethan-1-ol nonanoate | 250 |
| sucrose | 245 |

The above ingredients are thoroughly mixed and processed into single scored tablets, one tablet being administered every three to four hours.

EXAMPLE 13

| Ingredients | Quantity Per Tablet, mgs. |
| --- | --- |
| 2-(6,11-dihydrodibenzo-[b.e.]-thiepin-11-one-3-yl)ethan-1-ol dodecanoate | 150 |
| cornstarch | 100 |
| lactose | 368 |
| magnesium stearate | 2 |

The above ingredients are mixed intimately and pressed into single scored tablets.

EXAMPLE 14

| Ingredients | Quantity Per Capsule, mgs. |
| --- | --- |
| (dl)-2-(6,11-dihydrodibenzo-[b.e.]-thiepin-11-one-3-yl)propan-1-ol | 75 |
| lactose | 225 |
| dextrose | 10 |

The above ingredients are mixed and introduced into a hardshell gelatin capsule.

EXAMPLE 15

| Ingredients | Quantity Per Capsule, mgs. |
| --- | --- |
| (dl)-2-(6,11-dihydrodibenzo-[b.e.]-thiepin-11-one-3-yl)propan-1-ol acetate | 75 |
| lactose | 99 |

The above ingredients are mixed and introduced into a hardshell gelatin capsule.

EXAMPLE 16

| Ingredients | Quantity Per Tablet, mgs. |
| --- | --- |
| (dl)-2-(6,11-dihydrodibenzo-[b.e.]-thiepin-11-one-3-yl)propan-1-ol propionate | 75 |
| lactose | 135 |
| magnesium stearate | 5 |

The above ingredients are mixed and pressed into single scored tablets.

EXAMPLES 17

| Ingredients | Quantity Per Tablet, mgs. |
| --- | --- |
| (dl)-2-(6,11-dihydrodibenzo-[b.e.]-thiepin-11-one-3-yl)propan-1-ol hexanoate | 75 |
| cornstarch (paste) | 50 |
| magnesium stearate | 0.8 |
| lactose | to 500 |

The above ingredients are thoroughly mixed and pressed into single scored tablets.

EXAMPLE 18

| Ingredients | Quantity Per Tablet, mgs. |
| --- | --- |
| (dl)-2-(6,11-dihydrodibenzo-[b.e.]-thiepin-11-one-3-yl)propan-1-ol-nonanoate | 75 |
| cornstarch | 38 |
| magnesium stearate | 0.76 |
| polyvinylpyrrolidone | 17 |
| lactose | to 380 |

The above ingredients are mixed intimately and pressed into single scored tablets.

EXAMPLE 19

| Ingredients | Quantity Per Capsule, mgs. |
| --- | --- |
| (dl)-2-(6,11-dihydrodibenzo-[b.e.]-thiepin-11-one-3-yl)propan-1-ol dedecanoate | 75 |
| cornstarch | 38 |
| lactose | to 380 |

The above ingredients are mixed and introduced into a hardshell gelatin capsule.

EXAMPLE 20

| Ingredients | Quantity Per Capsule, mgs. |
| --- | --- |
| 2-(6,11-dihydrodibenzo-[b.e.]-thiepin-11-one-3-yl)ethan-1-ol tetrahydropyran-2'-yl ether | 150 |
| lactose | 72 |
| magnesium stearate | 8 |

The above ingredients are mixed and introduced into a hardshell gelatin capsule.

EXAMPLE 21

A suppository totaling 2.8 grams is prepared having the following composition:

| | |
| --- | --- |
| (dl)-2-(6,11-dihydrodibenzo-[b.e.]-thiepin-11-one-3-yl)propan-1-ol | 75 mg. |
| Witepsol H-15 (triglycerides of saturated vegetable fatty acids; a product of Riches-Nelson, Inc. | |

-continued

| | | |
|---|---|---|
| New York, N.Y.) | | balance |

EXAMPLE 22

An oral suspension for pediatric use is prepared having the following composition:

| | | |
|---|---|---|
| 2-(6,11-dihydrodibenzo-[b.e.]-thiepin-11-one-3-yl)ethan-1-ol | 2.25 | g. |
| fumaric acid | 0.5 | g. |
| sodium chloride | 2.0 | g. |
| methyl paraben | 0.1 | g. |
| granulated sugar | 25.5 | g. |
| sorbitol (70% solution) | 12.85 | g. |
| Veegum K (Vanderbilt Co.) | 1.0 | g. |
| flavoring | 0.035 | ml. |
| colorings | 0.5 | mg. |
| distilled water | to 100 | ml. |

EXAMPLES 23-24

Powdered top dressings for veterinary use are prepared having the following compositions:

| | Ex. 23 | Ex. 24 |
|---|---|---|
| 2-(6,11-dihydrodibenzo-[b.e.]-thiepin-11-one-3-yl)ethan-1-ol | 0.6 g. | 1.2 g. |
| sucrose | 5.7 g. | 3.7 g. |
| polyvinylpyrrolidone | 0.3 g. | 0.3 g. |

EXAMPLE 25

A suppository totaling 2.8 grams is prepared having the following composition:

| | |
|---|---|
| 2-(6,11-dihydrodibenzo-[b.e.]-thiepin-11-one-3-yl)ethan-1-ol | 825 mg. |
| Witepsol H-15 | balance |

EXAMPLE 26

The anti-inflammatory activity of the compounds embraced within this invention is determined by means of the carrageenin-induced rat paw inflammation assay described below.

ASSAY FOR ANTI-INFLAMMATORY ACTIVITY UTILIZING CARRAGEENIN INDUCED PAW INFLAMMATION IN THE RAT

Materials and Methods – Female rats weighing 80–90 grams are used. The test materials are given at hour 0 orally by gavage in 1 ml. aqueous vehicle. At hour 1, 0.05 ml. of a 1% solution (in 0.9% NaCl) of carrageenin is injected into the right hind paw. This injection causes an inflammation of the paw. The rats are sacrificed at hour 4, at which time both paws are removed and weighed separately.

End point: % increase in paw size calculated as follows:

$$\frac{\text{Wt. of Right Paw} - \text{Wt. of Left Paw}}{\text{Wt. of Left Paw}} \times 100$$

Results of initial assays for several of the compounds are summarized in the following table:

| Compound | Oral Anti-Inflammatory Activity Phenylbutazone = 1 |
|---|---|
| 2-(6,11-dihydrodibenzo-[b.e.]-thiepin-11-one-3-yl)ethan-1-ol | ~11 |
| 2-(6,11-dihydrodibenzo-[b.e.]-thiepin-11-one-3-yl)ethan-1-ol acetate | ~30 |
| 2-(6,11-dihydrodibenzo-[b.e.]-thiepin-11-one-3-yl)ethan-1-ol propionate | 10 |
| 2-(6,11-dihydrodibenzo-[b.e.]-thiepin-11-one-3-yl)ethan-1-ol hexanoate | 10 |
| 2-(6,11-dihydrodibenzo-[b.e.]-thiepin-11-one-3-yl)ethan-1-ol nonanoate | ~7 |

What is claimed is:

1. A compound selected from the group of compounds represented by the formulas:

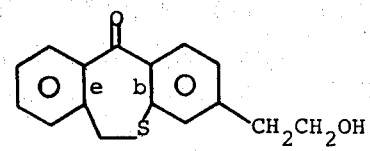

(A)

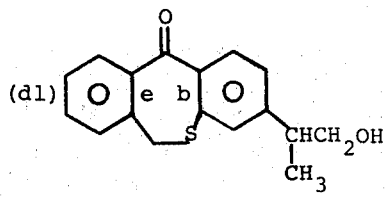

(B)

and the pharmaceutically acceptable esters and ethers thereof containing from 1 to 12 carbon atoms.

2. The compound of Formula (A) of claim 1, 2-(6,11-dihydrodibenzo-[b.e.]-thiepin-11-one-3-yl)ethan-1-ol.

3. The acetate of the compound of Formula (A) of claim 1, 2-(6,11-dihydrodibenzo-[b.e.]-thiepin-11-one-3-yl)ethan-1-ol acetate.

4. The propionate of the compound of Formula (A) of claim 1, 2-(6,11-dihydrodibenzo-[b.e.]-thiepin-11-one-3-yl)ethan-1-ol propionate.

5. The hexanoate of the compound of Formula (A) of claim 1, 2-(6,11-dihydrodibenzo-[b.e.]-thiepin-11-one-3-yl)ethan-1-ol hexanoate.

6. The nonanoate of the compound of Formula (A) of claim 1, 2-(6,11-dihydrodibenzo-[b.e.]-thiepin-11-one-3-yl)ethan-1-ol nonanoate.

7. The dodecanoate of the compound of Formula (A) of claim 1, 2-(6,11-dihydrodibenzo[b.e.]-thiepin-11-one-3-yl)ethan-1-ol dodecanoate.

8. The tetrahydropyran-2'-yl ether of the compound of Formula (A) of claim 1, 2-(6,11-dihydrodibenzo-[b.e.]-thiepin-11-one-3-yl)ethan-1-ol tetrahydropyran-2'-yl ether.

9. The compound of Formula (B) of claim 1, (dl)-2-(6,11-dihydrodibenzo-[b.e.]-thiepin-11-one-3-yl)propan-1-ol.

10. The acetate of the compound of Formula (B) of claim 1, (dl)-2-(6,11-dihydrodibenzo-[b.e.]-thiepin-11-one-3-yl)propan-1-ol acetate.

11. The propionate of the compound of Formula (B) of claim 1, (dl)-2-(6,11-dihydrodibenzo-[b.e.]-thiepin-11-one-3-yl)propan-1-ol propionate.

12. The hexanoate of the compound of Formula (B) of claim 1, (dl)-2-(6,11-dihydrodibenzo-[b.e.]-thiepin-11-one-3-yl)propan-1-ol hexanoate.

13. The nonanoate of the compound of Formula (B) of claim 1, (dl)-2-(6,11-dihydrodibenzo-[b.e.]-thiepin-11-one-3-yl)propan-1-ol nonanoate.

14. The dodecanoate of the compound of Formula (B) of claim 1, (dl)-2-(6,11-dihydrodibenzo-[b.e.]-thiepin-11-one-3-yl)propan-1-ol-dodecanoate.

15. The tetrahydropyran-2'-yl ether of the compound of Formula (B) of claim 1, (dl)-2-(6,11-dihydrodibenzo[b.e.]-thiepin-11-one-3-yl)propan-1-ol tetrahydropyran-2'-yl ether.

16. A compound selected from those represented by the formula:

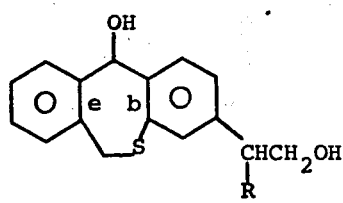

wherein R is hydrogen or methyl.

17. The compound of claim 16 wherein R is hydrogen, 2-(6,11-dihydrodibenzo-[b.e.]-thiepin-11-hydroxy-3-yl)ethan-1-ol.

18. The compound of claim 16 wherein R is methyl, (dl)-2-(6,11-dihydrodibenzo-[b.e.]-thiepin-11-hydroxy-3-yl)propan-1-ol.

19. A composition for treating inflammation, pain or pyrexia in mammals consisting essentially of a pharmaceutically acceptable non-toxic excipient and a therapeutically effective amount of a compound represented by the formulas:

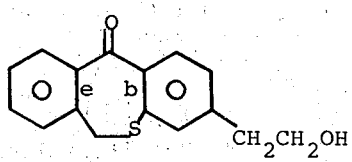

(A)

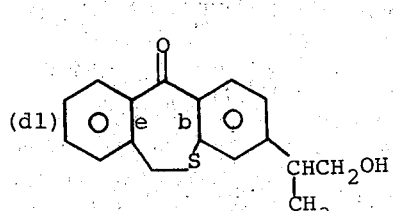

(B)

or a pharmaceutically acceptable ester or ether thereof containing from 1 to 12 carbon atoms.

20. A method of treating inflammation, pain or pyrexia in mammals which comprises administering to a mammal suffering therefrom a therapeutically effective amount of a compound represented by the formulas:

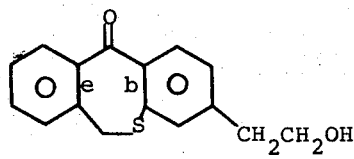

(A)

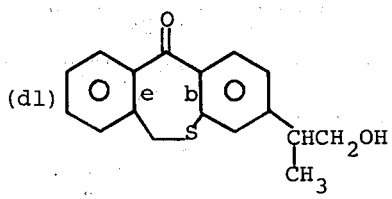

(B)

or a pharmaceutically acceptable ester or ether thereof containing from 1 to 12 carbon atoms.

21. A composition for administration to a pregnant mammal to delay the onset of parturition or to postpone parturition consisting essentially of a pharmaceutically acceptable nontoxic excipient and a therapeutically effective amount of a compound represented by the formulas:

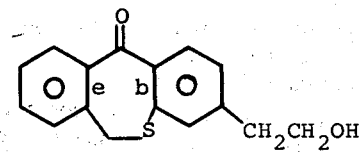

(A)

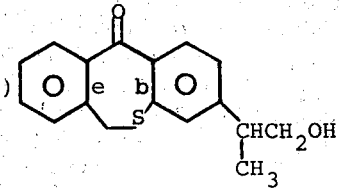

(B)

or a pharmaceutically acceptable ester or ether thereof containing from 1 to 12 carbon atoms.

* * * * *